United States Patent [19]

Tsuzuki et al.

[11] Patent Number: 4,695,644

[45] Date of Patent: Sep. 22, 1987

[54] PROCESS FOR PRODUCING PHENYL CHLOROTHIOFORMATES

[75] Inventors: Kenji Tsuzuki; Takeshi Uotani, both of Yamaguchi, Japan

[73] Assignee: Toyo Soda Manufacturing Co., Ltd., Tamaguchi, Japan

[21] Appl. No.: 862,923

[22] Filed: May 14, 1986

[30] Foreign Application Priority Data

May 14, 1985 [JP] Japan ............................ 60-100553
May 22, 1985 [JP] Japan ............................ 60-108290

[51] Int. Cl.$^4$ .......................................... C07C 68/00
[52] U.S. Cl. ................................................ 558/249
[58] Field of Search ..................................... 558/249

[56] References Cited

U.S. PATENT DOCUMENTS 3,165,544  1/1965  Tilles ................................. 558/249

FOREIGN PATENT DOCUMENTS 103963  9/1962  Czechoslovakia ................. 558/249

Primary Examiner—Henry R. Jiles
Assistant Examiner—Robert C. Whittenbaugh
Attorney, Agent, or Firm—Sughrue, Mion, Zinn Macpeak & Seas

[57] ABSTRACT

Phenyl chlorothioformates are produced in high yields easily and safely by (1) allowing sulfur dioxide to react with a mixed solution consisting of perchloromethyl mercaptan, an organic solvent and water, (2) removing the aqueous layer from the reaction mixture and (3) adding to the organic layer a phenol compound and a dehydrohalogenating agent in that order.

8 Claims, No Drawings

PROCESS FOR PRODUCING PHENYL CHLOROTHIOFORMATES

BACKGROUND OF THE INVENTION

1. Field of the Invention

This invention relates to a process for producing phenyl chlorothioformates. Phenyl chlorothioformates are very useful as intermediates for drugs and agricultural chemicals.

2. Description of Prior Art

It is known that phenyl chlorothioformates can be produced by reacting a phenol compound with thiophosgene in the presence of a dehydrohalogenating agent. However, since thiophosgene has a high toxicity, its handling requires great care. In view of the risk of such accidents as leakage, it is desirable to avoid the storage or transfer of thiophosgene in large quantity. Hence, the present inventors previously proposed a process for producing phenyl chlorothioformates by allowing sulfur dioxide to react with a mixed solution consisting of a phenol compound, perchloromethyl mercaptan, an organic solvent and water and then adding a dehydrohalogenating agent thereto. In this process, however, a phenoxydichloromethanesulfenyl chloride is formed as a by-product, whereby the yield of phenyl chlorothioformates is reduced.

SUMMARY OF THE INVENTION

The object of the present invention is to avoid the storage or transfer of thiophosgene in large quantity and to enable production of phenyl chlorothioformates in high yields easily and safely.

According to the present invention, there is provided a process for producing phenyl chlorothioformates in high yields by (1) allowing sulfur dioxide to react with a mixed solution consisting of perchloromethyl mercaptan, an organic solvent and water, (2) removing the aqueous layer from the reaction mixture and (3) adding to the organic layer a phenol compound and a dehydrohalogenating agent in that order.

Other object and advantages of the present invention will become apparent to those skilled in the art from the following description and disclosure.

DETAILED DESCRIPTION OF THE PREFERRED EMBODIMENTS

Perchloromethyl mercaptan is added to a mixed solvent consisting of an organic solvent and water, to obtain a mixed solution, said mercaptan being at least 1 mole, preferably at least 1.1 mole, based on 1 mole of a phenol compound.

The organic solvent includes chlorinated hydrocarbons (e.g. chloroform, dichloromethane, carbon tetrachloride), aromatic hydrocarbons (e.g. benzene, toluene, xylene), etc. It is desirable to use water in an amount of at least about 2 moles based on 1 mole of perchloromethyl mercaptan. A small amount of an alkali metal iodide can be added in order to allow the reaction to proceed smoothly.

In allowing sulfur dioxide to react with the mixed solution, sulfur dioxide is directly bubbled into the mixed solution, or a sulfite and concentrated sulfuric acid are added to the mixed solution to generate sulfur dioxide in the reaction system. In the former case, sulfur dioxide is used in an amount of about 1 to 20 moles based on 1 mole of perchloromethyl mercaptan. In the latter case, the sulfite is used in an amount of at least about 1 mole based on 1 mole of perchloromethyl mercaptan and concentrated sulfuric acid is used in an amount of at least about 1/10 mole based on 1 mole of perchloromethyl mercaptan.

As the sulfite, there can be used alkali metal hydrogensulfites (e.g. sodium hydrogensulfite, potassium hydrogensulfite), alkali metal sulfites (e.g. sodium sulfite, potassium sulfite), ammonium hydrogensulfite and ammonium sulfite.

Next, the aqueous layer is removed from the reaction mixture, and to the remaining organic layer are added a phenol compound and a dehydrohalogenating agent in that order.

As the phenol compound, there can be used nonsubstituted phenols, alkyl-substituted phenols (e.g. methylphenol, ethylphenol, tert-butylphenol) and condensation phenols (e.g. β-naphthol, 5,6,7,8-tetrahydro-2-naphthol).

As the dehydrohalogenating agent, there can be mentioned inorganic bases such as alkali metal hydroxides, alkaline earth metal hydroxides, alkali metal carbonates and the like, as well as organic bases such as triethylamine, pyridine, quinoline, isoquinoline and the like. The dehydrohalogenating agent is used in an amount of about 1 mole based on 1 mole of phenol.

The dehydrohalogenating agent can be used ordinarily in a solution form. The dehydrohalogenating agent concentration in the solution has a close connection with the yields of phenyl chlorothioformates. Use of a solution containing the dehydrohalogenating agent in a high concentration generates diphenyl thiocarbonate as a by-product and reduces the yields of phenyl chlorothioformate. On the other hand, use of a solution containing the dehydrohalogenating agent in too low a concentration necessitates the adoption of a reactor of large capacity, which is disadvantageous. Hence, the dehydrohalogenating agent concentration in the solution is preferably about 5 to 20% by weight.

The reaction temperature is preferably about −10° C. to room temperature in ordinary cases.

The reaction time can ordinarily be within about 10 hours.

Thus, phenyl chlorothioformates can be produced in high yields easily and safely by (1) allowing sulfur dioxide to react with a mixed solution consisting of perchloromethyl mercaptan, an organic solvent and water, (2) removing the aqueous layer from the reaction mixture and (3) adding to the organic layer a phenyl compound and a dehydrohalogenating agent in that order.

The present invention will be explained specifically below by way of Examples. However, the present invention is in no way restricted only to these Examples.

EXAMPLE 1

Into a 1-liter, three-necked flask equipped with a stirrer, a thermometer and a 300-ml dropping funnel were charged 150 g of perchloromethyl mercaptan, 240 ml of carbon tetrachloride, 240 ml of water and 1 g of potassium iodide. The flask was ice-cooled.

150 g of sulfur dioxide was bubbled into the above solution while being stirred. The temperature inside the flask was kept at 0° C. to 10° C.

Then, the water layer was removed from the reaction mixture, and to the remaining organic layer were added dropwise 90 g of 3-tert-butylphenol and 290 ml of a 10% aqueous sodium hydroxide solution in that order. After completion of the addition, stirring was continued for a further 2 hours. After completion of the reaction, the organic layer was separated from the reaction mixture and subjected to distillation to obtain 130 g of 3-tert-butylphenyl chlorothioformate. The yield of this product was 94.8% based on 3-tert-butylphenol.

COMPARATIVE EXAMPLE 1

Into a 1-liter, three-necked flask equipped with a stirrer, a thermometer and a 300-ml dropping funnel were charged 60 g of 3-tert-butylphenol, 75 g of perchloromethyl mercaptan, 240 ml of carbon tetrachloride, 240 ml of water and 3 g of potassium iodide. The flask was ice-cooled.

100 g of sulfur dioxide was bubbled into the above solution while being stirred. The temperature inside the flask was kept at 0° C. to 10° C.

Then, the water layer was removed from the reaction mixture, and to the remaining organic layer was added dropwise 42 ml of a 40% aqueous sodium hydroxide solution.

After completion of the addition, stirring was continued for a further 2 hours. After completion of the reaction, the organic layer was separated from the reaction mixture and subjected to distillation to obtain 46.6 g of 3-tert-butylphenyl chlorothioformate. The yield of this product was 51% based on 3-tert-butylphenol.

EXAMPLES 2 to 5

A phenol compound and other substances, all shown in Table 1, were charged into the same apparatus as used in Example 1 and subjected to reaction under the conditions shown in Table 1. Then, the same treatment as in Example 1 was applied to obtain the respective phenyl chlorothioformate products shown in Table 1.

The results are shown in Table 1.

for 10 hours. The temperature inside the flask was kept at 0° C. during the addition and at room temperature thereafter.

The water layer was removed from the reaction mixture, and to the remaining organic layer were added dropwise 80 g of 4-methylphenol and 320 ml of a 10% aqueous sodium hydroxide solution in that order. Stirring was conducted for a further 2 hours.

After completion of the reaction, the organic layer was separated from the reaction mixture and subjected to distillation to obtain 110.6 g of 4-methylphenyl chlorothioformate. The yield of this product was 80% based on 4-methylphenol.

COMPARATIVE EXAMPLE 2

Into a 1-liter, three-necked flask equipped with a stirrer, a thermometer and a 300-ml dropping funnel were charged 85 g of 4-methylphenol, 147 g of perchloromethyl mercaptan, 290 g of sodium hydrogensulfite, 150 ml of dichloromethane, 250 ml of water and 3 g of potassium iodide. The flask was ice-cooled.

3.5 ml of concentrated sulfuric acid was added dropwise to the above solution, and stirring was conducted for 25 hours. The temperature inside the flask was kept at 0° C. during the addition and at room temperature thereafter.

The water layer was removed from the reaction mixture, and to the remaining organic layer was added dropwise 315 ml of a 10% aqueous sodium hydroxide solution. Stirring was continued for a further 2 hours.

After completion of the reaction, the organic layer was separated from the reaction mixture and subjected to distillation to obtain 85.2 g of 4-methylphenyl chlorothioformate. The yield of this product was 58.0% based on 4-methylphenol.

TABLE 1

| | Phenols (g) | Perchloromethyl mercaptan (g) | Solvents (ml) | Water (ml) | Sulfur dioxide (g) | Iodides (g) | Dehydrohalogenating agents (ml) | Reaction temp. (°C.) | Reaction time (hr) | Phenyl chlorothioformates (g) |
|---|---|---|---|---|---|---|---|---|---|---|
| Ex. 2 | Phenol 85 | 185 | Benzene 100 | 280 | 220 | — | 8% sodium hydroxide 540 | 5 to 10 | 8 | Phenyl chlorothioformate 109.1 |
| Ex. 3 | 5,6,7,8-Tetrahydro-2-napthol 95 | 131 | Chloroform 250 | 250 | 130 | Potassium iodide 2 | 10% potassium hydroxide 420 | 0 to 10 | 5 | 5,6,7,8-Tetrahydro-2-napthyl-chlorothioformate 130.8 |
| Ex. 4 | 4-Methylphenol 80 | 165 | Dichloromethane 150 | 250 | 140 | Sodium iodide 2.5 | 15% sodium hydroxide 245 | −10 to 10 | 6 | 4-Methylphenyl chlorothioformate 127.1 |
| Ex. 5 | 4-Ethylphenol 90 | 140 | Carbon tetrachloride 250 | 250 | 145 | Potassium iodide 1.5 | 8% sodium hydroxide 445 | 5 to 10 | 6 | 4-Ethylphenyl chlorothioformate 118.5 |

EXAMPLE 6

Into a 1-liter, three-necked flask equipped with a stirrer, a thermometer and a 300-ml dropping funnel were charged 160 g of perchloromethyl mercaptan, 210 g of sodium hydrogensulfite, 200 ml of carbon tetrachloride, 250 ml of water and 2 g of potassium iodide. The flask was ice-cooled.

25 ml of concentrated sulfuric acid was added dropwise to the above solution, and stirring was conducted

EXAMPLES 7 to 10

A phenol compound and other substances, all shown in Table 2, were charged into the same reactor as used in Example 1 and subjected to reaction under the conditions shown in Table 2. The same treatment as in Example 2 was then applied to obtain the phenyl chlorothioformate products shown in Table 1.

The results are shown in Table 2.

TABLE 2

| | Phenols (g) | Perchloromethyl mercaptan (g) | Sulfites (g) | Iodides (g) | Conc. sulfuric acid (ml) | Solvents (ml) | Water (ml) | Dehydrohalogenating agents (ml) | Reaction temp. (°C.) | Reaction time (hr) | Phenyl chlorothioformates (g) |
|---|---|---|---|---|---|---|---|---|---|---|---|
| Ex. 7 | 3-Tert-butylphenol 80 | 130 | Sodium hydrogensulfite 210 | Sodium iodide 2 | 20 | Chloroform 200 | 180 | 10% potassium hydroxide 330 | 0 to 20 | 20 | 3-Tert-butylphenyl chlorothioformate 98.5 |
| Ex. 8 | 5,6,7,8-Tetrahydro-2-napthol 80 | 125 | Sodium hydrogensulfite 200 | Potassium iodide 3 | 20 | Dichloromethane 180 | 200 | 15% sodium hydroxide 160 | −10 to 20 | 15 | 5,6,7,8-Tetrahydro-2-napthyl chlorothioformate 99.2 |
| Ex. 9 | Phenol 70 | 150 | Sodium sulfite 310 | — | 30 | Benzene 150 | 200 | 10% sodium hydroxide 330 | 0 to 30 | 24 | Phenyl chlorothioformate 51.5 |
| Ex. 10 | 4-Ethylphenol 90 | 135 | Sodium hydrogensulfite 220 | Sodium iodide 3 | 25 | Carbon tetrachloride 170 | 170 | 10% sodium hydroxide 320 | 0 to 25 | 18 | 4-Ethylphenyl chlorothioformate 96.2 |

What is claimed is:

1. A process for producing a phenyl chlorothioformate, which comprises (1) allowing sulfur dioxide to react with a mixed solution consisting of perchloromethyl mercaptan, an organic solvent and water, (2) removing the water layer from the reaction mixture and (3) adding to the remaining organic layer a phenol compound or condensed phenol and a dehydrohalogenating agent in that order.

2. The process of claim 1 wherein the mixed solution optionally contains a small amount of an alkali metal iodide.

3. The process of claim 1 wherein the dehydrohalogenating agent concentration in the solution is about 5 to 20% by weight.

4. The process in claim 2 wherein the dehydrohalogenating agent concentration in the solution is about 5 to 20% by weight.

5. The process in claim 1 wherein the reaction temperature is about −10° C. to room temperature.

6. The process in claim 2 wherein the reaction temperature is about −10° C. to room temperature.

7. The process in claim 3 wherein the reaction temperature is about −10° C. to room temperature.

8. The process in claim 4 wherein the reaction temperature is about −10° C. to room temperature.

* * * * *